US005479969A

United States Patent [19]
Hardie et al.

[11] Patent Number: 5,479,969
[45] Date of Patent: * Jan. 2, 1996

[54] APPARATUS FOR DISPENSING SUBSTANCES WHICH ARE BIOLOGICALLY HAZARDOUS

[75] Inventors: Robert Hardie, Warrington; Kevin Shaw, Great Sutton, both of United Kingdom

[73] Assignee: British Nuclear Fuels plc, Warrington, United Kingdom

[*] Notice: The portion of the term of this patent subsequent to May 10, 2011, has been disclaimed.

[21] Appl. No.: 211,811

[22] PCT Filed: Aug. 13, 1993

[86] PCT No.: PCT/GB93/01718

§ 371 Date: Jul. 7, 1994

§ 102(e) Date: Jul. 7, 1994

[87] PCT Pub. No.: WO94/04415

PCT Pub. Date: Mar. 3, 1994

Related U.S. Application Data

[63] Continuation-in-part of Ser. No. 933,373, Aug. 24, 1992, Pat. No. 5,309,959.

[30] Foreign Application Priority Data

Aug. 19, 1992 [GB] United Kingdom ............ 9217616
Mar. 22, 1993 [GB] United Kingdom ............ 9305882

[51] Int. Cl.⁶ ............................................. B65B 43/42
[52] U.S. Cl. ............... 141/130; 141/98; 141/103; 422/99; 422/100
[58] Field of Search ............ 141/130, 97, 98, 141/103, 104, 329, 330; 901/8, 16, 31; 422/99, 100, 102

[56] References Cited

U.S. PATENT DOCUMENTS 4,131,426 12/1978 Range ............................. 141/1
4,854,355 8/1989 Chazot et al. ................ 141/130
4,862,932 9/1989 Feinstein et al. .............. 141/130
4,869,299 9/1989 Handke .............................. 141/1
4,922,782 5/1990 Kawai ............................. 901/8 X
5,067,532 11/1991 Lang et al. ..................... 141/329
5,102,623 4/1992 Yamamoto et al. ........ 141/130 X
5,132,088 7/1992 Wakatake ................... 141/130 X Primary Examiner—Henry J. Recla
Assistant Examiner—Timothy L. Maust
Attorney, Agent, or Firm—William R. Hinds

[57] ABSTRACT

A dispensing apparatus comprises a robot device (14) having gripping means (20a, 20b) presentable to a plurality of stations, each station being adapted to provide an operation in a sequence of operations such as to produce a measured quantity or dose from a supply of a hazardous substance, and one of the stations (32) comprising a multi-syringe receiving and filling station comprising syringe receiving means (106) capable of receiving and holding syringes of different sizes each adapted to contain a said substance, the said station having means (95) for operating each syringe when located at that station whereby syringes of different sizes may be operated automatically as selected. The said station may comprise a hazardous liquid filling station for filling items one of which comprises a syringe. The hazardous substance dispensed by the apparatus may comprise a radionuclide, a cytotoxin, a chemotherapeutic agent or a dangerous substance containing one or more bacteriological or viral ingredients or material used in positron emission topography. The said sequence of operations including operations at the filling station may include operations to: (a) elute material from a concentrated source to a user stock source, e.g. in a stock bottle; (b) preparation of different strength doses from the stock source; and (c) preparation of individual patient doses from the appropriate selected doses.

20 Claims, 8 Drawing Sheets

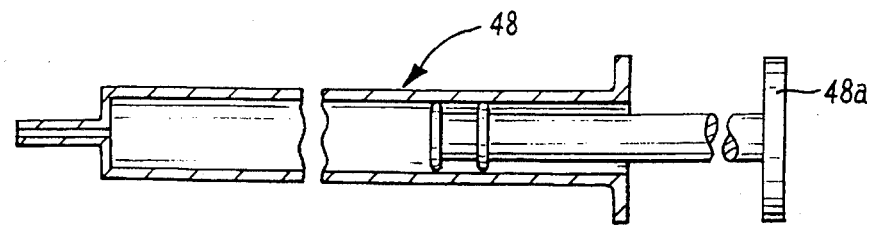
_Fig.2_
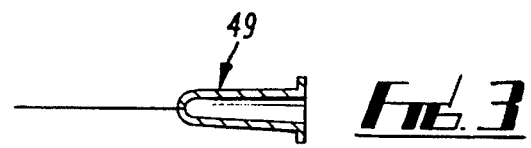
_Fig.3_
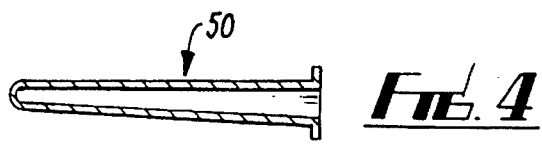
_Fig.4_
_Fig.5_
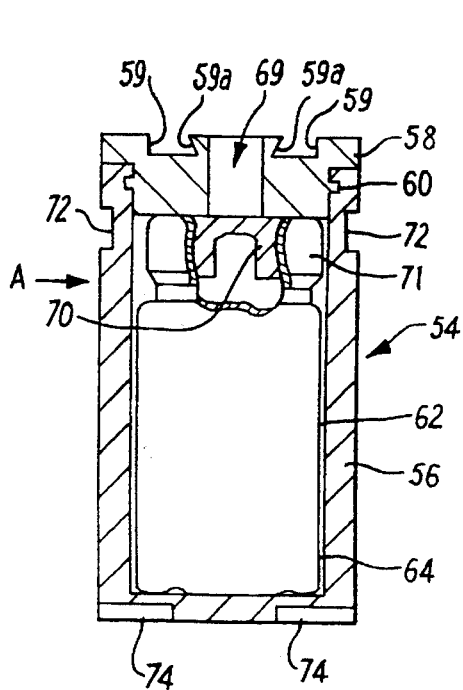
_Fig.6_
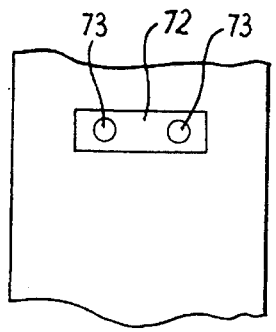
_Fig.6a_
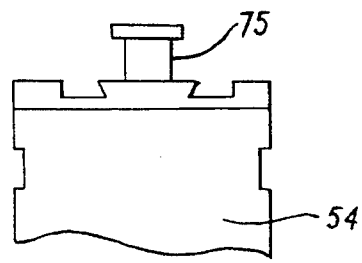
_Fig.6b_

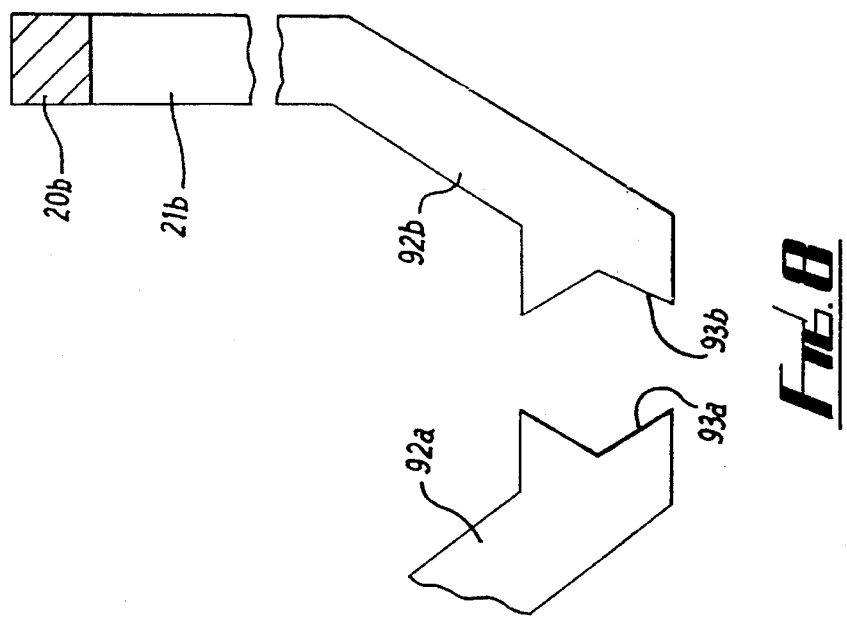
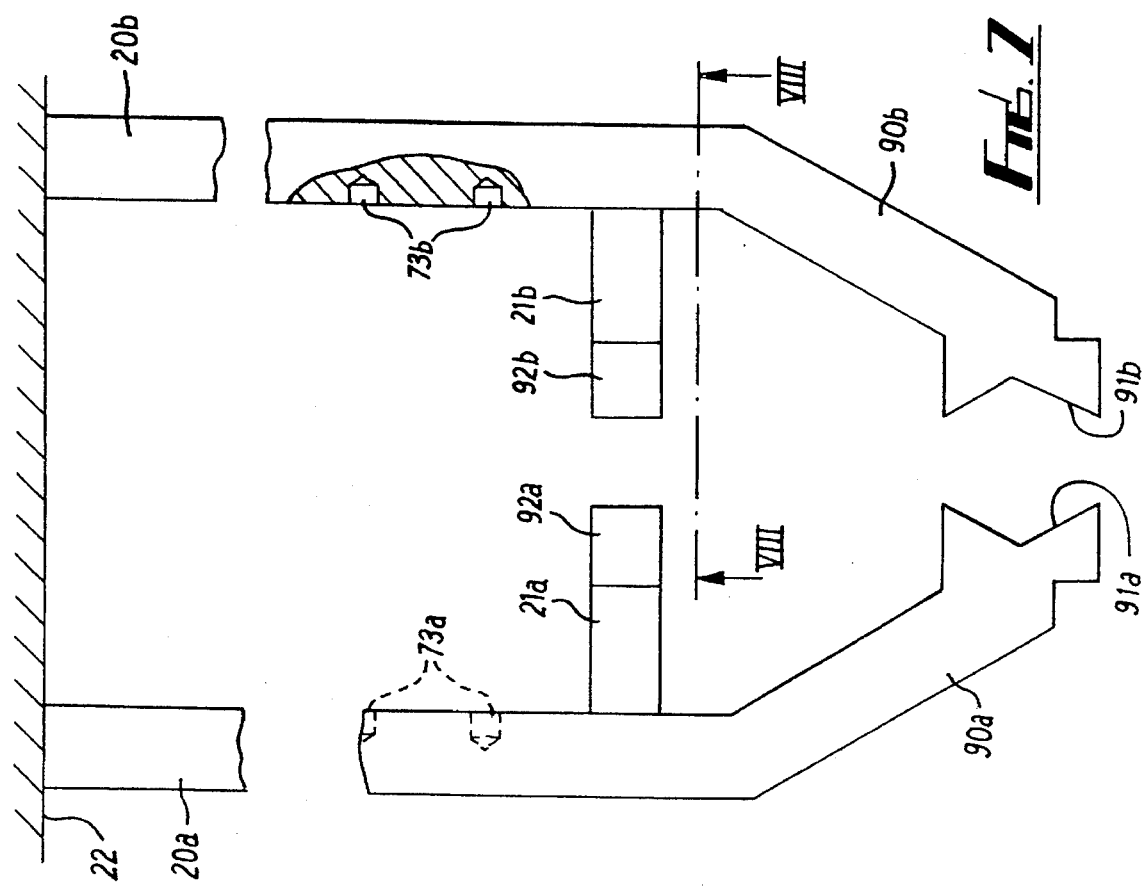

APPARATUS FOR DISPENSING SUBSTANCES WHICH ARE BIOLOGICALLY HAZARDOUS

This application is a continuation-in-part of U.S. application Ser. No. 07/933,373, now U.S. Pat. No. 5,309,959, filed Aug. 24, 1992.

The present invention relates to dispensing apparatus, particularly apparatus for dispensing substances which are biologically hazardous, i.e. substances which are hazardous to humans or other living species and can cause biological damage to such living species if they come into contact with such substances in an uncontrolled manner.

There are a range of different substances which fall into the category of biologically hazardous materials and these include radioisotopes, chemotherapeutic agents, cytotoxins and substances containing one or more bacteriological or viral ingredients. Such materials are employed in a variety of useful applications and their storage and handling therefore has to be managed with extreme care.

For example, radioisotopes are today employed in an increasing range of processes in the fields of food preparation, agriculture, water supply and biological and industrial research. One of the most important uses of these elements is in the field of medicine, where radioisotopes of elements such as iodine and technetium have become important tools in the diagnosis and also increasingly in the treatment of various conditions.

The uses of radioisotopes in clinical medicine can be grouped into two main categories, both of which can be referred to under the broad heading of "radio pharmaceuticals". These categories are:

(a) diagnostic pharmacology; and (b) radiotherapy.

Diagnostic radioisotopes are used as markers within the body. They may be used in the free form allowing the body's handling of the elements to be traced, but more often they are attached to selected molecules as a "label" or "tracer" allowing the passage and distribution of these molecules to be traced in the body.

The range of tracers available to medicine has now expanded to allow specific examination of, for example, the kidney, liver, heart, brain, lung and thyroid gland.

Therapeutic radioisotopes can be implanted surgically into malignant tumours to deliver radiation directly to cancerous cells, as in radium therapy for breast cancer or they can be attached to biologically active molecules to seek out tumour cells in particular body tissues.

Whilst some of these agents can be manufactured under controlled conditions by the pharmaceutical companies, a large number are made up in hospital pharmacies or commercial dispensaries when needed. The radioisotopes most desired for diagnostic purposes usually have a short half life and emit a significant amount of radiation during the period of use.

The dangers of ionising radiation are well known and apply to all persons coming into contact with radiation. However, the staff involved in preparation of radio pharmaceuticals are exposed to an additional risk posed by the selectivity of the radio labels.

In hospital pharmacies or dispensing establishments radioisotope-containing compositions are normally prepared as liquids manually in what is an exacting but tedious responsibility for highly skilled staff. The substances concerned may be highly radioactive as well as highly toxic and even for skilled staff the preparations represent extremely hazardous operations.

It is, therefore, an object of the invention to provide an automated dispenser to simplify and to carry out without operator involvement the operations normally carried out manually for preparing doses or controlled quantities containing potentially biologically hazardous substances whilst maintaining the exacting standards set by regulatory bodies.

According to the present invention there is provided a dispensing apparatus comprising a robot device having gripping means presentable to a plurality of stations, each station being adapted to provide an operation in a sequence of operations such as to produce a measured quantity or dose from a supply of a hazardous substance, and one of the stations comprising a multi-syringe receiving and filling station comprising syringe receiving means capable of receiving and holding syringes of different sizes each adapted to contain a said substance, the said station having means for operating each syringe when located at that station.

The said syringe receiving and filling station may comprise multiple ports in parallel for receiving and filling syringes of different sizes. Each such port may include its own syringe locating and operation means. Alternatively, the apparatus may comprise a single port having a single syringe locating and operation means, the locating means being adjustable so as to receive syringes of different sizes.

The said station may comprise a hazardous liquid filling station for filling items one of which comprises a syringe. Various examples of filling steps by the filling station are described further below.

The said station may further comprise at the or each port where a syringe may be located and held means for locating a container and means for moving the container toward the syringe, whereby one end of the syringe enters the container.

The said station may further include means for equalising the air pressure in the syringe and the container when one is inserted into the other. The said station may also include means for rotating the syringe port relative to the container location means whereby in use the container may be arranged to be above the syringe. In that position the plunger of the syringe in the port may thereafter be operated by its own separate device forming part of the filling station mechanism to withdraw hazardous liquid contained in the container into the syringe. The syringe port may subsequently be rotated relative to the container location means so that the syringe is once more above the container. Alternatively, where the syringe already contains liquid, the liquid may be transferred to a container without the rotation step.

Syringes for use in connection with the apparatus according to the present invention may each have shoulders for supporting the syringe and a plunger for drawing liquid into and ejecting liquid from the syringe and the liquid filling station may comprise a mechanism providing at the or each syringe port:

(a) means for locating the shoulders of the syringe in use at the port;

(b) means for locating and operating in use the plunger of the syringe;

(c) means for locating in use the upper end of a container and for resiliently opposing relative movement of the container and syringe; and (d) means for inverting the container relative to the syringe.

Where the syringe receiving and filling station comprises a single port the means for locating the syringe shoulders may comprise one or more abutment members having an adjustable aperture through which syringes of different diameter may be fitted to be retained on the abutment member(s) by the syringe shoulders, the size of the aperture being selected according to the size of syringe presented. The adjustable aperture may be provided by resilient, e.g. spring loaded, jaws in the abutment member.

Syringes of different length may be accommodated by the abutment members which retain the shoulders on the syringe being adjustable in their mutual spacing. For example, one of the abutment members may be adjustable in position by a motorised drive, the position being selected according to the required length of syringe selected.

In general, syringes of different sizes will have different lengths and diameters.

In the operations described above the syringe may have a needle fitted into its end which pierces a cap in the container.

The multi-syringe receiving and filling station beneficially allows syringes of different sizes to be used. Where the station comprises a single port different syringes are received and filled at different times. This may also be the case where multiple ports are provided although, if required, more than one syringe may be filled at the same time in parallel.

The hazardous substance might comprise a potentially biologically damaging substance, such as a radionuclide or a cytotoxin or a chemotherapeutic agent or a dangerous substance containing one or more bacteriological or viral ingredients or a material used in the known technique of positron emission tomography (pet) used for X-ray investigations. The measured dose transferred at the filling station might be retained in a said syringe, or in a medical vial.

Preferably, means are provided for controlling the apparatus especially the robotic device in a predetermined sequence of operations. The means for controlling may comprise a computer, e.g. a personal digital computer, which may also control performance of other operations relating to use of the apparatus as described below. The operations controlled in the sequence may also include operation of the mechanisms at the filling station and operation of a lift or elevator device at a radiation monitor station.

The computer may provide to a known logic controller which operates the various mechanisms of the robotic device a series of control signals which cause the robotic device and the other mechanisms to perform a series of operations according to a pre-determined routine sequence. The computer may issue an initialising routine signal whereby wherever the arm of the robotic device is positioned when the robotic device is first energised the arm is first returned to the same reference position before the operating routine is begun.

The robotic device may be controlled such that after one lifting operation has been completed by the robotic device the device may begin another lifting operation without delay. An operation at the workstation on the item deposited there, e.g. radioactivity monitoring or liquid filling at the filling station, may be carried out at the same time as the next operation of the robotic device. This avoids unnecessary delay in the operational sequence.

The workstations may be disposed radially about the robotic device to facilitate access thereto by the gripping means.

The gripping means may comprise fingers which are adapted to pick up different items e.g. bottles or syringes at their ends or between their sides. The fingers may have side projections which themselves can be used to pick up further items either at their ends or between their sides when the first mentioned fingers have been rotated through 90°.

The apparatus according to the present invention may be fully enclosed within a hood or cover which may for example include a strong transparent portion, e.g. made of polymethylmethacrylate. The purpose of such a hood is to isolate the operations inside the hood from the environment outside. The environment outside may itself be a clean room. The hood may be adapted to prevent: (a) operator injury by the robotic device; (b) spread of airborne substances; and (c) contamination of the substances being prepared by the apparatus. The enclosure within the hood may be ventilated to prevent the ingress of contaminants such as bacteria. The air drawn into the enclosure may be passed through a suitable filter, e.g. a so-called HEPA filter. There may be a control preventing operator access into the enclosure within the hood whilst the apparatus is energised for use.

The workstations visited by the robotic device may comprise:

(a) one or more hazardous substance sources;

(b) one or more trays or pallets holding unused syringes and vials and optionally syringe and vial caps and shielded vial storage and/or transportation containers;

(c) a liquid filling station where the contents of a syringe may be discharged into a vial or withdrawn from a vial as appropriate;

(d) a solution radioactivity monitoring station;

(e) a waste disposal station which may include a needle removal means for selective disposal of needles;

(f) a vial turnover station;

(g) a vial shield de-lidding station.

The hazardous source may comprise a radioisotope generator or, where the substance is a non-radioactive substance, a stock solution containing the substance, e.g. chemotherapeutic agent.

Where the apparatus according to the present invention is a radioisotope or other hazardous substance dispenser it may provide the following procedures each involving a plurality of sequenced operations:

(1) elution: drawing from a source of the radioisotope or other hazardous substance, e.g. pet material, a measured quantity of liquid containing the radioisotope or other material and adding the quantity to one or more other ingredients, e.g. saline solution, to form a stock solution;

(2) multi-dose preparation: drawing from the stock solution a measured quantity and adding that to one or more ingredients for producing different desired concentrations of solution for specific types of treatment application e.g. target substances for particular organs;

(3) preparation of patient doses: drawing samples from the multi-dose composition (for a particular organ treatment for example), diluting them as required to form doses to meet the specific requirements of individual patients.

Where the apparatus according to the present invention is a non-radioactive substance dispenser, e.g. for a chemotherapeutic substance, the procedures it performs may be similar to procedures (1) and (2) described above for radioisotopes.

The various procedures (1), (2) and (3) described above may themselves include the following steps:

(1) Elution (a) an empty stock bottle is picked up by the robotic device;

(b) the stock bottle is presented by the robotic device to the port from which the radioisotope or other hazardous material, e.g. pet material, at its source may be drawn; and a quantity of the radioisotope or hazardous material is drawn into the stock bottle;

(c) the stock bottle and its contents are transferred by the robotic device to a storage station, e.g. a storage tray, where the bottle is stored until required for use.

Between steps (a) and (b) the stock bottle may be moved by the robotic device to a turnover station where the bottle is turned over by the robotic device and then regripped by the robotic device for presentation to the source of hazardous material.

Desirably, the stock bottle is in a shielded container whilst it is being moved for the elution procedure and is stored in the shielded container having a lid placed thereon. The lid may be removed at a de-lidding station which may be adjacent to the turnover station.

The elution procedure may be carried out at set times, e.g. at the start of operations on each day. A radioactivity monitoring step may be carried out on samples of the eluted stock shortly after elution and if required at other times. Such a step may be carried out in three stages. Firstly, the overall activity of the stock solution is measured; next the specific activity of a known quantity of the stock solution is measured and finally a shielded sample of the solution is monitored to check for so-called "molybdenum breakthrough". These stages are described further below.

(2) Multi-Dose Preparation (a) a syringe is collected by the robotic device;

(b) the syringe is placed and fitted in the appropriate port in the filling station by the robotic device;

(c) the stock bottle with eluted stock solution is placed below the syringe at the filling station by the robotic device;

(d) the stock bottle is raised by the filling station mechanism so that the syringe enters the stock bottle;

(e) the syringe and stock bottle are rotated by the filling station mechanism so that the stock bottle is above the syringe;

(f) a quantity of the stock solution is withdrawn by the filling station mechanism from the stock bottle into the syringe;

(g) the stock bottle is returned by the robotic device to its position on a storage tray;

(h) a multi-dose preparation vial is placed by the robotic device beneath the syringe; this may for example contain a targeting agent for examination of a specific organ; and (i) the contents of the syringe are transferred into the vial by the filling station mechanism.

Desirably, the syringe has a sheathed needle whose protective sheath is removed (by the robotic device) before placing the syringe on the filling station port in step 2(b).

Desirably, the said vial is moved inside a radiation shield. Desirably, the stock bottle is always in its shield when it is being moved except during two stages of radioactivity monitoring as described below. As noted above, the stock bottle is preferably lidded whilst being stored and so its lid requires removal by the robotic device before step (c) and after step (g).

Desirably, the radioactivity of the multi-dose preparation is monitored (by the monitor device to which it is transferred by the robotic device) after the transfer in step (g) after which the multi-dose preparation is transferred by the robotic device to a storage tray where it is stored in a shielding container. Desirably, after the above steps the syringe, needle and sheath are disposed of by the robotic device at a waste disposal station. Desirably, during the liquid transfer proceudre but prior to step (e) air is injected into the stock bottle so that pressures in the syringe and bottle are equalised prior to step (e).

Preparation of a sample of known volume of the stock solution formed in the elution procedure for radioactivity monitoring purposes may be carried out using steps similar to those used in multi-dose preparation. Thus, a small measured quantity of the stock solution is transferred into a vial in a manner similar to steps (a) to (i) of procedure 2. The vial is then transferred by the robot device to a radioactivity monitoring station where the specific activity of the measured quantity of solution is measured. Contamination by molybdenum of the solution may also be detected at the radioactivity monitoring station in a known way by remeasuring the radioactivity of the measured solution quantity using a suitable molybdenum radiation shield.

(3) Patient Dose Preparation (a) a syringe is collected and placed by the robotic device in the or the appropriate port of the filling station as in steps 2(a) and (b).

(b) an appropriate multi-dose vial is placed by the robotic device below the syringe and raised so that the syringe enters the vial; this step is carried out by the filling station mechanism;

(c) the syringe and vial are rotated by the filling station mechanism so that the vial is above the syringe;

(d) the contents of the vial are drawn into the syringe by the filling station mechanism;

Desirably, air is added to the vial by the filling station mechanism before step (c) so that pressures in the vial and syringe are equalised.

Desirably, the syringe is monitored for radioactivity after filling in step 3(c) (in the same manner as described above). Desirably, the vial is returned to its storage tray by the robotic device after step 3(c). Desirably, a sheathed needle is picked up by the syringe on the robotic device and the sheath is removed before the placing of the syringe at the filling station in step 3(a). Such a needle sheath may be refitted on the needle after step (d) and transferred by the robotic device to the waste disposal station where the needle and sheath may be removed from the syringe and disposed of; this may be achieved using a fixed collar at that station into which the needle and sheath are positioned whereby the needle and sheath are removed at the collar by lifting of the syringe by the robotic device. Desirably, a fresh sheathed needle is fitted to the end of the syringe thereafter by the robotic device and the syringe and sheathed needle are deposited in an appropriate shielded container (e.g. on a tray of containers) for subsequent removal and transport to a patient. The container may have a identity designation, e.g. bar code, and details of the patient and dose corresponding to the designation may be stored by computer (which may be the same as that controlling the sequence of operations). Subsequent automatic labelling of the container from a printer connected to the computer may be carried out by reading the designation, e.g. using a bar code optical reader device.

The apparatus according to the present invention has been demonstrated successfully as a working prototype and has been shown to have the following benefits:

(a) the risk of error is minimised; there is a greater accuracy and better consistency of doses compared with equivalent manual operation;

(b) where the hazardous substance is radioactive the radioactive dose to operators is minimised; this meets so-called "ALARP" principles for radiation exposure; no human contact is made with hazardous substances;

(c) efficiency is enhanced; 40 doses per hour can typically be produced by one apparatus; automatic operation using the apparatus according to the present invention allows better utilisation of trained staff;

(d) non-scheduled dose preparation may be achieved;

(e) consistent accurate dose preparation may be achieved;

(f) a permanent and compact record of all activities carried out by the apparatus may be carefully controlled in a computer database;

(g) contamination of sterile items used in the preparation of doses is minimised.

Embodiments of the present invention will now be described by way of example with reference to the accompanying drawings, in which:

FIG. 1 shows a perspective diagrammatic representation of a dispensing apparatus;

FIGS. 2 to 5 shown in median section a conventional hypodermic syringe and items associated therewith;

FIG. 6 shows to an enlarged scale a median sectional view of a vial shield containing a medical vial;

FIG. 6a shows a fragmentary view in the direction of arrow 'A' of FIG. 6;

FIG. 6b shows a fragmentary view of a modification to the vial shield of FIG. 6;

FIG. 7 shows a plan view to an enlarged scale of jaws for the apparatus of FIG. 1;

FIG. 8 shows a view on the line VIII—VIII of FIG. 7;

Figure 1:
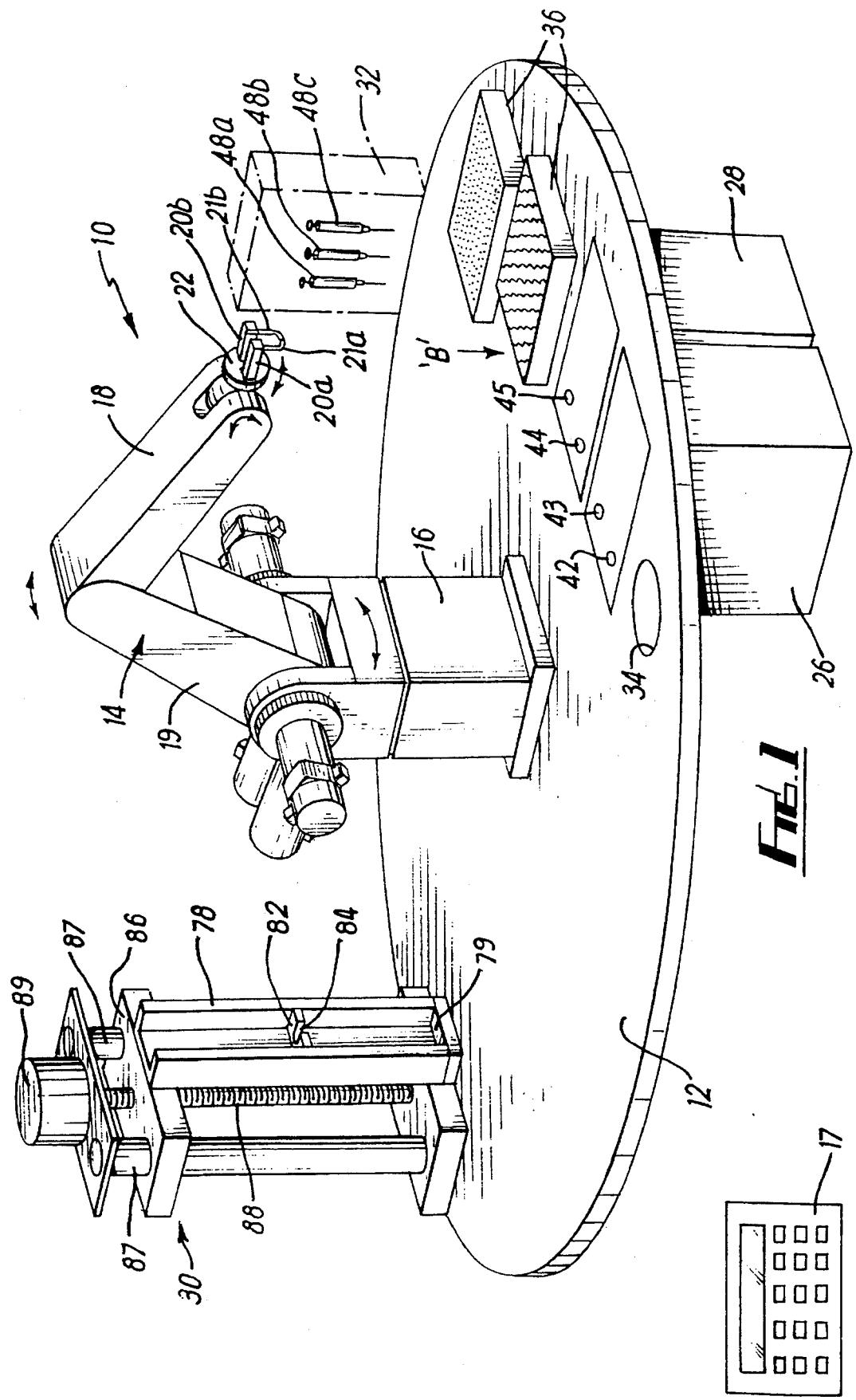

Referring now to FIG. 1, an automatic dispenser 10 is inside a shielded arrangement in a clean room (not shown). The dispenser 10 comprises a base or table 12 having thereon an industrial robot device 14 rotatable on a plinth 16 mounted on the base 12 and is controlled to provide desired movements and operations by a digital computer 17 acting through a logic controller of a known kind (not shown). The robot device 14 has articulated arms 18, 19, and a rotatable wrist elements 22 on the arm 18. Gripping means acting like fingers are attached to the wrist element 22. In FIG. 1 the means are shown as jaw members 20a, 20b having respective depending tangs 21a, 21b. Alternative forms for the gripping means are described below with reference to FIGS. 12, 13, 14 and 15.

The robot device 14 is arranged to present the gripping means comprising the members 20a, 20b at a number of operation stations in the form of: radioisotope generators 26, 28 respectively, a monitor station 30, a multi-port syringe operating assembly or filling station 32 (shown only in phantom outline), a waste disposal station 34, and trays 36 for holding or storing items to be handled by the dispenser 10.

The generators 26, 28 are proprietary items supplied by companies such as Amersham International, Amersham, United Kingdom, or Dupont, or Mallinkrodt, for the supply of a specific radioisotope, e.g. commercial sources of technetium 99m, thallium, gallium, indium, rhenium or iodine 131 or substances of similar nature. Each generator 26, 28 has respective needle-type socket connectors 42, 44, and rotary control valves 43, 45, and usually the generators 26, 28 are arranged so that they supply the radioisotope at different radioactive decay states.

A suitable robot device 14 is that manufactured by: CRS Plus Inc 830 Harrington Court, Burlington, Ontario, Canada L7N 3N4, and distributed in the United Kingdom by: Affordable Automation Ltd, PO Box 31, Eccles, Manchester, M30 7QB.

Referring now to FIGS. 2 to 6 various items suitable for handling by the dispenser 10 are shown, namely a hypodermic syringe 48 having a plunger 48a, a hypodermic needle 49 for the syringe 48, a sheath 50 for the needle 49, a medical hub 53 for fitting on to the end of the syringe 48 without the needle 49 thereon, and a vial shield form of which is shown as a vial shield 54 (another form is as described with reference FIG. 16 below). Different sizes of syringes 48, and vial shields 54 (with vials therein) may be used in different procedures as explained below.

Figure 11:
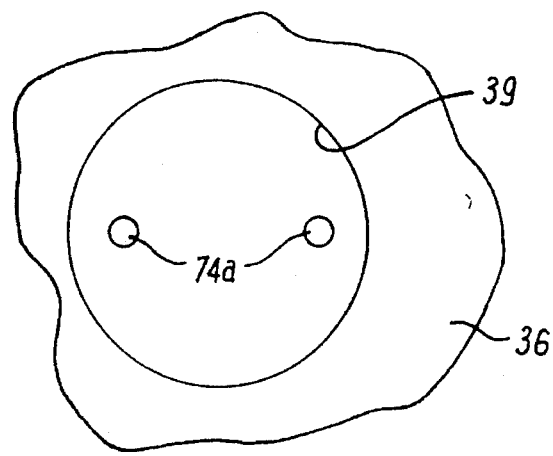
FIG. 11 shows to an enlarged scale a view in the direction of arrow 'B' of FIG. 1.

Each vial shield 54 comprises a pot 56 having a cap 58 secured by a bayonet-type catch 60 to the pot 56, and arranged to contain a conventional medical vial 62. The cap 58 has parallel grooves 59 with inward wedge-shaped faces 59a which complement the shape of the jaws 20a, 20b. A hole 69 in the cap 58 allows access to a rubber sealing plug 70 retained by a captive metal cap 71 in the vial 62. Two peripheral grooves 72 in the side of the vial shield 54 assist in handling of the vial shields 54 by the jaws 20a, 20b, and two pins 73 in each groove 72 (see FIG. 6a) assist retention of the jaws 20a, 20b. Two slots 74 on a common diameter extend from either side in the base of the vial shield 54 to locate corresponding pins 74a in holes 39 in some of the trays 36 (see FIG. 11). The vial 62 might be an empty bottle, or a bottle containing a powder intended to dissolve in a liquid injected into the bottle, or a bottle containing a medical saline solution. The vial shield 54 is preferably made of tungsten, but might be lead with a protective coating. An alternative vial shield 54 or monitoring for molybdenum is shown in FIG. 6a and is similar to the vial shield 54 of FIG. 6 except that the hole 69 is omitted and a handle 75 provided. Referring again to FIG. 1, the monitor station 30 comprises a recessed slide 78 having a lower platform 79, and an intermediate support 82 having a slot 84 to locate one of the syringes 48. The slide 78 is joined at its upper end to a table 86 located on guide rods 87, and arranged to be moved vertically by a lead screw 88. The lead screw 88 is operated by a motor 89 so as to lower the slide 78 into a conventional lead shielded, radioactivity detector (not shown) beneath the table 12.

One form of the gripping members comprising the jaws 20a, 20b for use with the vial shields 54 (shown in FIG. 6) is shown in FIGS. 7 and 8. The jaw members 20a, 20b, have inwardly shaped ends 90b, 90b with opposing V-shaped grip portions 91a, 91b. The depending tangs 21a, 21b have inwardly formed ends 92a, 92b with opposing V-shaped grip portions 93a, 93b. Holes 73a, 73b in the jaws 20a, 20b respectively are arranged to locate the pins 73 of the vial shields 54, 54a, and the outer edges of the grip portions 91a, 91b are arranged to fit into the grooves 59 of the vial shields 54, 54a.

Figure 9:
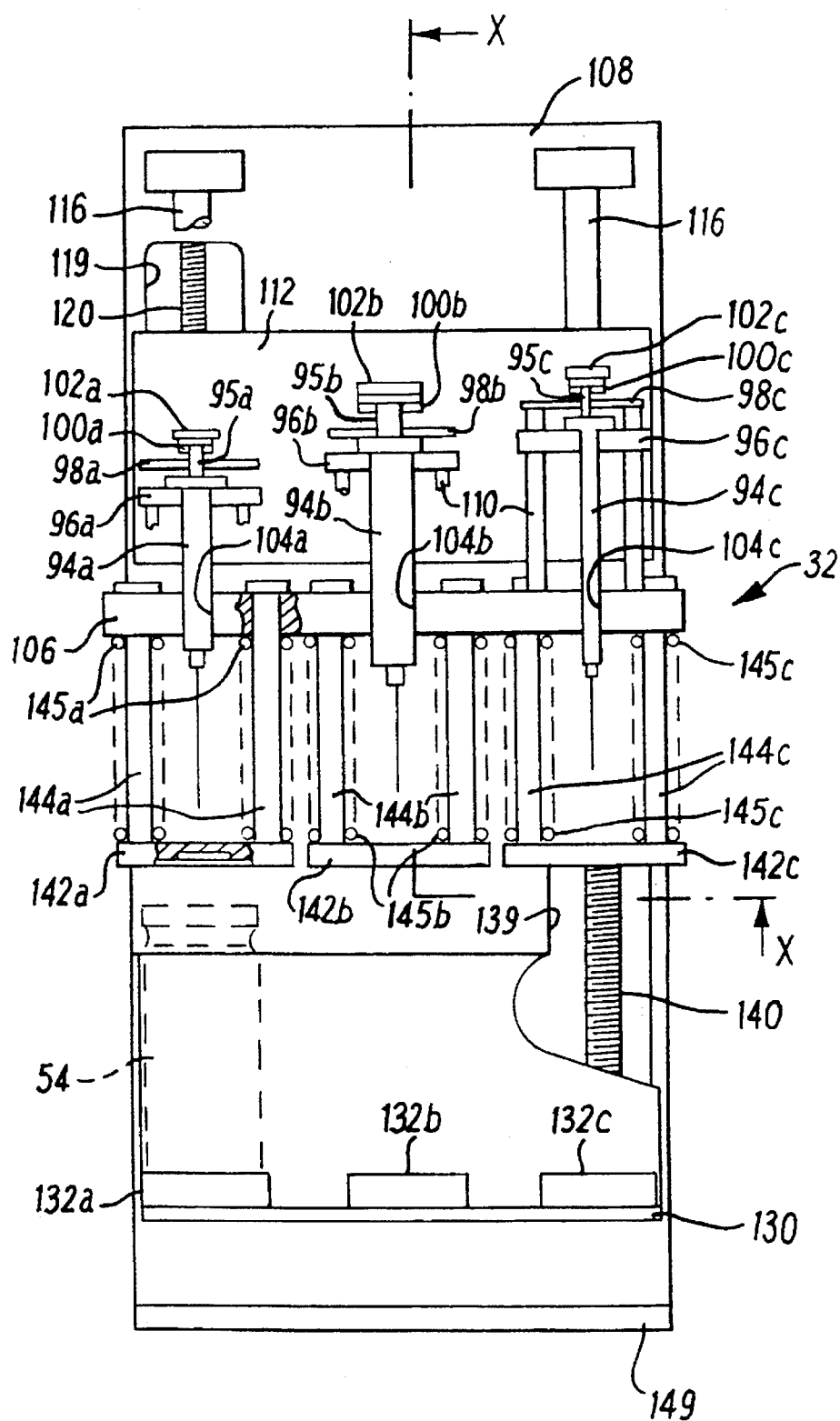
FIG. 9 shows a front view in part section and to an enlarged scale of a syringe operating assembly for the apparatus of FIG. 1.
Figure 10:
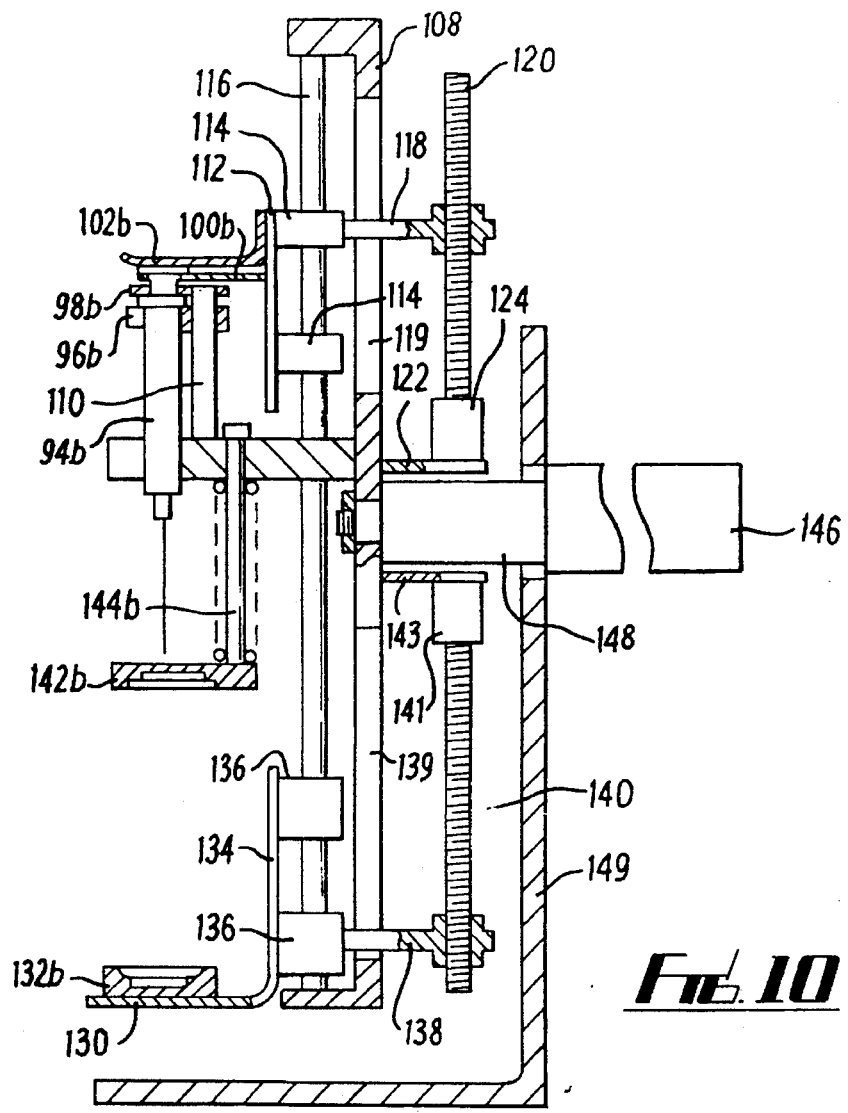
FIG. 10 shows a view on the line X—X of FIG. 9.

A preferred multi-port syringe operating assembly or filling station 32 is shown in FIGS. 9 and 10 to which reference is made. The station 32 is arranged to locate three syringes 94a, 94b, 94c respectively of different capacities on slotted lower shoulders 96a, 96b, 96c where they are retained by slotted upper shoulders 98a, 98b, 98c respectively. The syringes 94a, 94b and 94c are shown together but in practice they are desirably used separately in operations which take place at different times. Plungers 95a, 95b, 95c of the syringes 94a, 94b, 94c respectively locate on lower slotted tangs 100a, 100b, 100c and are retained by upper tangs 102a, 102b, 102c respectively. The bodies of the syringes 94a, 94b, 94c extend through respective slots 104a, 104b, 104c in a block 106 secured to an upright wall 108. The lower shoulders 96a, 96b, 96c and the upper shoulders 98a, 98b, 98c are secured to the block 106 through upright support rods 110. The lower tangs 100b, 100b, 100c and the upper tangs 102a, 102b, 102c are supported from one side of an upright plate 112 mounted on linear bearings 114 that slide on two parallel columns 116 supported by the wall 108. An offset arm 118 from an outermost linear bearing 114 extends through an elongate slot 119 in the wall 108, and locates in engagement with a lead screw 120 driven by a motor 124 supported on a bracket 122 from the wall 108 so as to raise and lower the plate 112. A platform 130 has three recessed bases 132a, 132b, 132c respectively to locate vial shields 54 or vials 62, and is shaped to define an upright rear portion 134 mounted by linear bearings 136 on the columns 116. To raise and lower the platform 130, an offset arm 138 extends from an outermost linear bearing 136 through a slot 139 in the wall 108 to engage a lead screw 140 which is separately driven by a motor 141 supported on a bracket 143 from the wall 108. Upper locators 142a, 142b, 142c are supported from the block 106 by sets of slide rods 144a, 144b, 144c respectively. A spigot 148 supported by a stand 149 and rotatable by a motor 146 supports the wall 108 so as to be capable of inverting the wall 108.

In use of the dispenser 10 the procedures of elution, multi-dose preparation and patient dose preparation may be carried out in the manner described above. The required radioisotope may for example be technetium 99.

Syringes 48, vial shields 54, needles 49, sheaths 50, hubs 53, vials 62 etc. used in these operations may be stored on the trays 36.

At the start of operations on each day elution is carried out. The robot device 14 picks up an empty vial 62 places it in a vial shield 54 and then moves the shield 54 containing the vial 62 to a turnover station (not shown) on the table 12 where the shield 54 and vial 62 inside is turned over. The inverted shield 54 containing the vial 62 is then re-gripped by the device 14 and a lid on the shield 54 may be removed and deposited at a de-lid station adjacent to the turnover station. The shield 54 and vial 62 are then presented to a selected radioisotope generator 26 or 28. The vial shield 54 is pressed downward so that the needle of the socket connector 42 or 44 penetrates the hole 69 and the rubber plug 70 of the vial 62. The vial 62 is usually under vacuum so that liquid containing a radionuclide is sucked from the respective generator 26, 28 into the vial 62 to provide a stock solution therein. The vial 62 in its shield 54 is extracted, re-lidded, re-inverted and placed on one of the storage trays 36.

The stock solution contents of the vial 62 is monitored after filling of the vial 62.

Firstly, the vial 62 without its shield 54 is placed on the lower platform 79 of the monitor station 30 which is then lowered to the radioactivity detector to measure the specific radioactivity of the stock solution. Next, the specific activity of a known quantity of the stock solution is measured and compared with the expected activity for that quantity calculated by the computer 17.

A known small quantity, e.g. 1 cm$^3$, of the stock solution is transferred to an empty small vial 62 in the manner used for multi-dose preparation as described below. That small vial 62 is placed by the robot device 14 unshielded 54 on the lower platform 79 where it is lowered to the radioactivity detector for radioactivity monitoring thereby. Finally, the small vial 62 is subsequently removed from the platform 79 and placed in the vial shield 54a to which the handle 75 is fitted to complete the shielding around the small vial 62. It is then replaced on the lower platform 79 by the device 14 for further monitoring at the radioactivity detector. This step allows contamination by molybdenum caused by so-called "molybdenum break-through" in the solution eluted as the stock solution to be detected. Any such molybdenum will emit radiation which will penetrate the shield 54a and be detected by the radioactivity detector.

After the monitoring step has been carried out the small vial 62, its contents (a small amount of the stock solution) and the shield 54a are disposed of by the robotic device 14 at the waste disposal station 34.

After monitoring and before use, the shielded vial 62 containing the stock solution closed with a shielding lid is stored on the tray 36.

In another operation the dispenser 10 is used for multi-dose preparation, i.e. preparation of solutions of different concentration from which multiple doses at the required concentration can subsequently be produced. The shielded vial 62 containing the stock solution is delidded and then transferred by the robot device 14 to the platform 130 (FIGS. 9 and 10) where it is placed on the appropriate base, e.g. 132a. A syringe (e.g. 94a) of the appropriate capacity is fitted by the robot device 14 with a needle 49 from which the sheath 50 has been removed and then fitted into an appropriate port in the station 32 by the robot device 14 to be retained therein in the manner described with reference to FIGS. 9 and 10. The platform 130 is raised so that the needle 49 of the syringe 94a pierces the vial 62 in the vial shield 54. Air is injected into the vial 62 by operation of the plunger 95a to equalise air pressures in the vial 62 and in the syringe 94a. The wall 108 is inverted by the motor 146, and the syringe plunger 95a is lowered by the tangs 100a, 100b so as to withdraw liquid from the vial 62 and expel liquid into the syringe 94a. The wall 108 is inverted again, the platform 130 is lowered, and the vial shield 54 containing the stock solution vial 62 is removed and placed in one of the trays 36. Another vial 62 containing a targeting agent for examination of a specific organ is next picked up by the robot device 14 and placed on the appropriate base, e.g. 132a, of the port of the filling station 32 holding the liquid-containing syringe 94a. The vial 62 is raised so that it is penetrated by the needle 49. The plunger 95a is again operated and the liquid in the syringe 94a is transferred into the empty vial 62. The syringe 94a is picked up again by the robot device 14 and its previously removed sheath 50 is replaced on the needle 49. The robot device 14 next transfers the used syringe 94a together with its needle 49 and sheath 50 to the waste disposal station where they are disposed of. Finally, the radioactivity of the solution added to the vial 62 is monitored in the manner described above and the vial 62 containing the targeting agent plus added radioactive solution is placed in a shielded container on one of the trays 36.

A measured dose for a patient may be extracted from a multi-dose preparation vial 62 by placing the vial 62 on the appropriate tray, e.g. 132c, on the platform 130 by the robot device 14, locating a fresh syringe 94c, suitable for containing a patient dose, with its needle 49 from which the sheath 50 has been removed in the appropriate port in which it fits in the filling station 32 by the robot device 14, raising the platform 130 so that the needle 49 penetrates the vial 62, equalising air pressure in the vial 62 and the syringe 94c, inverting the vial 62 relative to the syringe 94c, depressing the plunger 95a to withdraw solution from the vial 62 into the syringe 94c. Further steps carried out by the robot device 14 include replacing the vial 62 in its shielded container on one of the trays 36, replacing the needle 49 and sheath 50 on the syringe 48c and transporting them to the waste disposal station where the needle 49 and sheath 50 are removed, fitting a fresh needle 49 and sheath 50 thereon on the syringe 48c. Finally, the syringe 48c with its fresh needle 49 and sheath 50 is transferred by the device 14 to a transport container (not shown) and stored to await transport (usually on the same day) to an individual patient. The patient dose may be labelled by an operation controlled by the computer 17 so as to show the identity of the patient and for the dose.

It will be understood that in the above procedures where transfer of liquid using syringes 94a at the filling station 32 is carried out.

The wall 108 may be inverted several times to agitate the vial 62. It will be understood that a similar procedure will be followed for a syringe 94b, 94c.

Appropriate fittings (not shown) may be attached to the trays 36 to hold the vial shields 54, or sheaths and enable the robot device 14 to remove and replace the cap 58, etc. Shielded receptacles (not shown) may be located in the trays 36 to locate the loaded syringes 94a, 94b, 94c, vials 62, etc.

Preferred linear bearings are those made by THK Co Ltd, Tokyo 141, Japan, and obtainable inter alia from:

(1) Unimatic Engineering Ltd 122 Granville Road London NW2 2LN United Kingdom (2) THK America Inc 1300 Landmeier Road Elk Grove Village Illinois 60007 United States of America If dose dilution is required, saline solution may be withdrawn from an appropriate vial 62 by use of the syringe 48, and then inserted into a required vial 62 at the filling station 32 in the manner used for patient dose preparation.

Non-nuclear pharmaceutical doses may be dispensed by the dispenser 10, for example doses containing cytotoxins. The radiopharmaceutical uses of the dispenser 10 may relate to diagnostic and radiotherapeutic applications.

Figure 12:
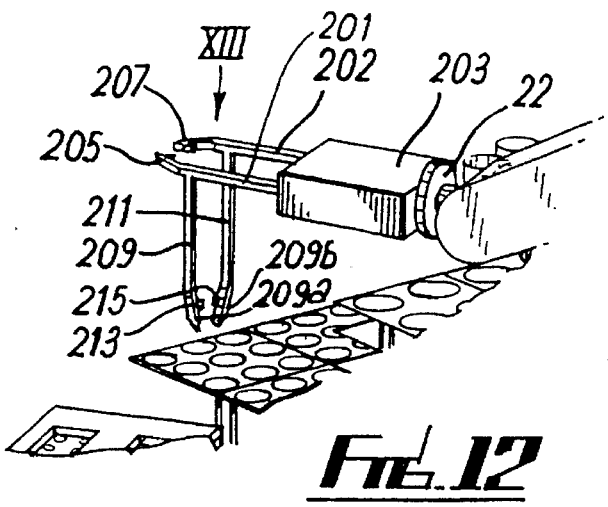
FIG. 12 is a perspective view of alternative gripping means for the robotic device of-the apparatus shown in FIG. 1.
Figure 13:
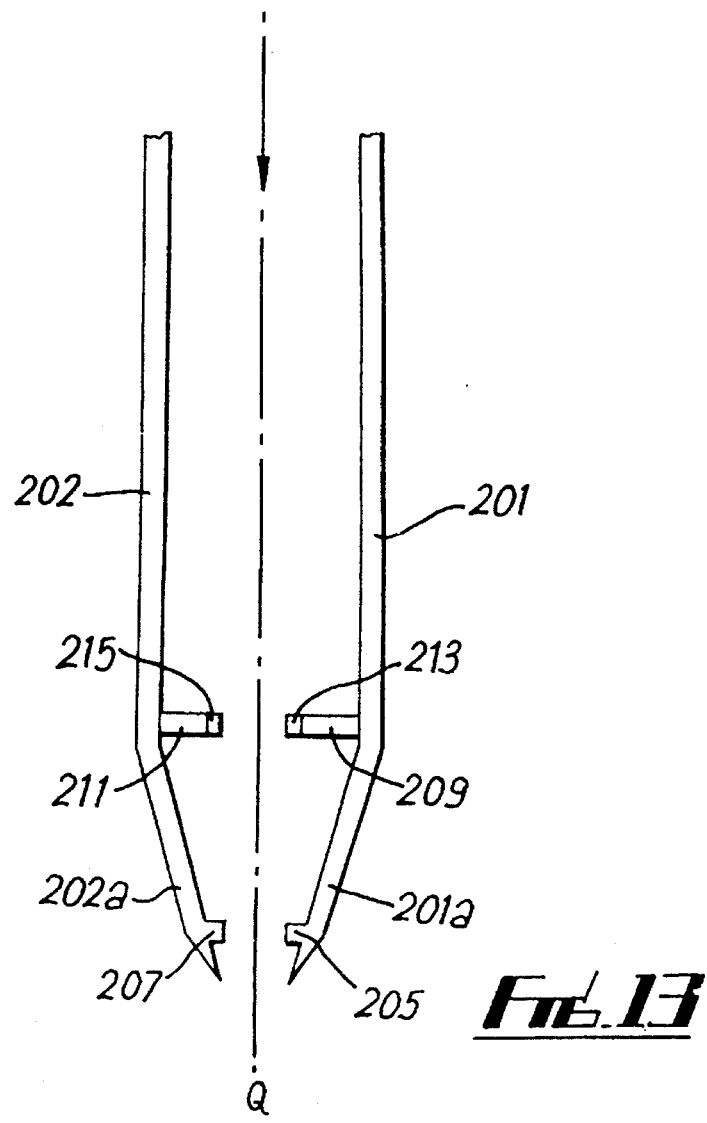
FIG. 13 is a plan view in the direction XIII of the gripping means shown in FIG. 12.

FIGS. 12 and 13 show an alternative form of gripping means for the robot device 14 shown in FIG. 1 instead of joint members 20a and 20b. In FIGS. 12 and 13 fingers 201, 202 having a rectangular cross-section are rigidly fitted in a block 203 which may be rotated by the wrist element 22 (FIG. 1). The fingers 201, 202 extend along an axis Q parallel to the axis about which rotation of the wrist element 22 takes place. Near their free ends the fingers 201, 202 have inwardly inclined portions 201a, 202a so that their ends which are bevelled inwardly are relatively close together. Inward facing tangs 205, 207 projecting from the portions 201a, 202a facilitate picking up of small objects. Fingers 209, 211 project from the fingers 201, 202 along an axis at right angles to the axis of the fingers 201, 202.

The fingers 209, 211 have ends similar to those of the fingers 201, 202, viz inwardly inclined portions 209a, 209b having inwardly bevelled ends and inward facing tangs 213,215 projecting therefrom. The fingers 201, 202 and the fingers 209, 211 allow objects to be picked up at their respective tangs along two mutually orthogonal axes, i.e. parallel to or perpendicular to the axis of rotation if the wrist element 22, the required axis being chosen by computer control of the rotation of the wrist element 22.

Figure 14:
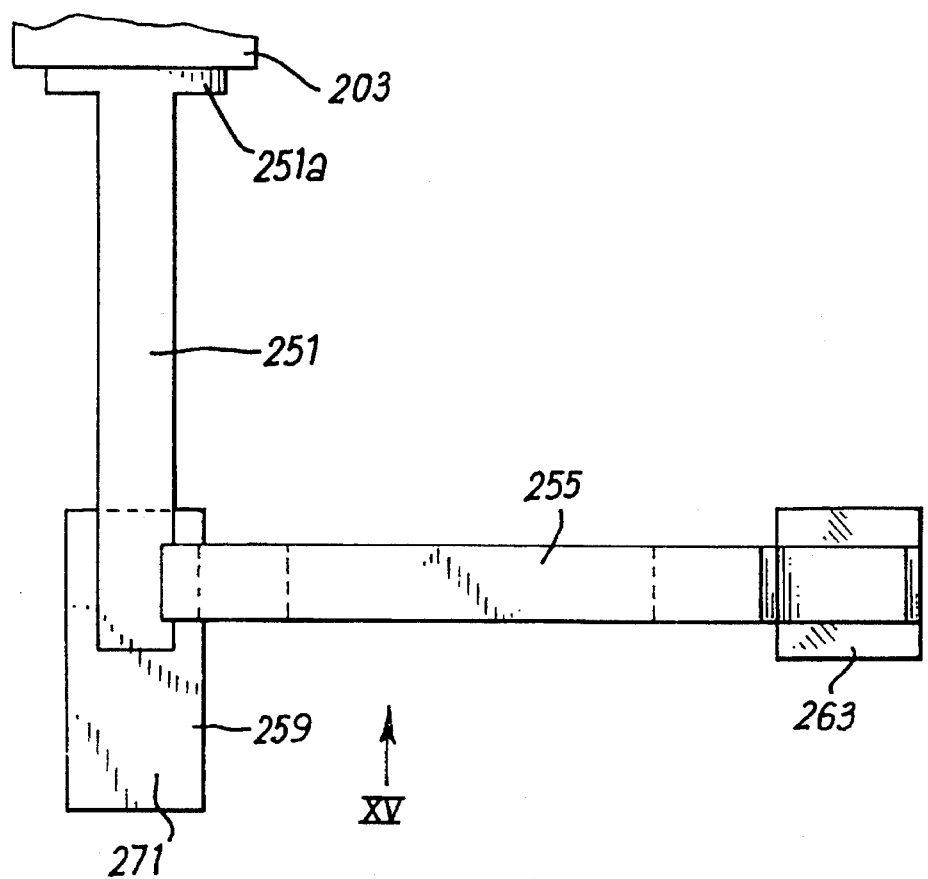
FIG. 14 is a plan view and FIG. 15 is a side view in the direction XV in FIG. 14 of further alternative gripping means for the robotic device of the apparatus shown in FIG. 1.
Figure 15:
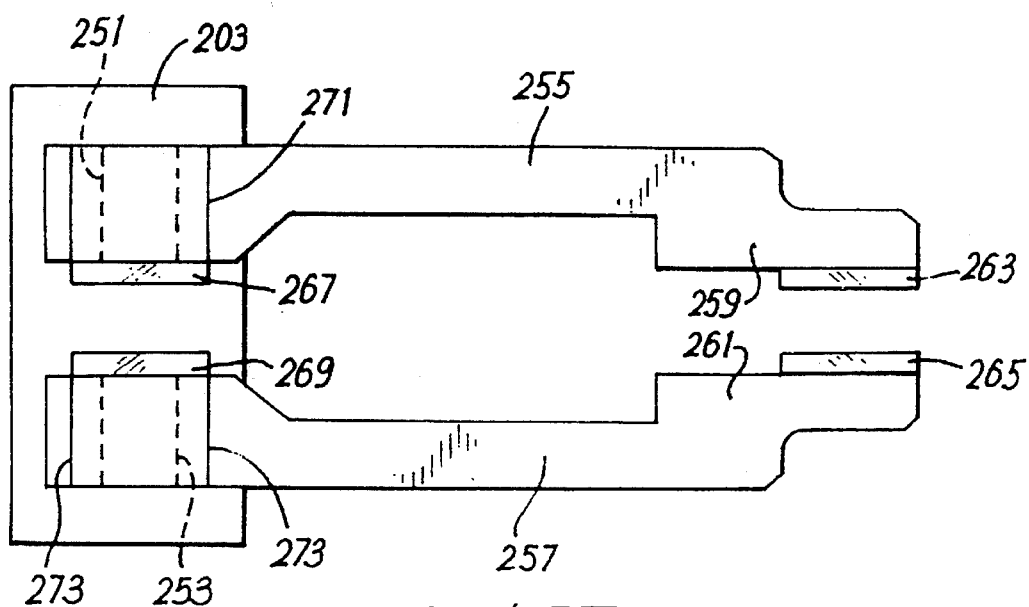

Shown in FIGS. 14 and 15 is a further alternative form for the gripping means of the robotic device 14. The fingers 201, 202, 209 and 211 in FIGS. 12 and 13 are replaced by rods 251, 253 having projections 255, 257 rigidly attached to and extending therefrom orthogonal to the rods 251, 253. The rods 251, 253 are attached to the block 203 (the same as in FIG. 12) which in turn is rotatable by the wrist element 22 (FIG. 12) by flanges 251a, 253a (the latter not shown).

The projections 255, 257 are stepped to form neighbouring gripping portions 259, 261 having flat square plates 263, 265 to provide complementary jaw surfaces. Similar square flat plates 267, 269 forming another pair of jaw surfaces are provided on end blocks 271, 273 attached to the rods 251, 253.

The jaws formed by the plates 263,265 and those formed by the plates 267, 269 allows objects to be picked up along mutually orthogonal axes, i.e. parallel to or perpendicular to the axis of rotation of the wrist element 22, the required axis being selected by computer control of the rotation of the wrist element 22.

Figure 16:
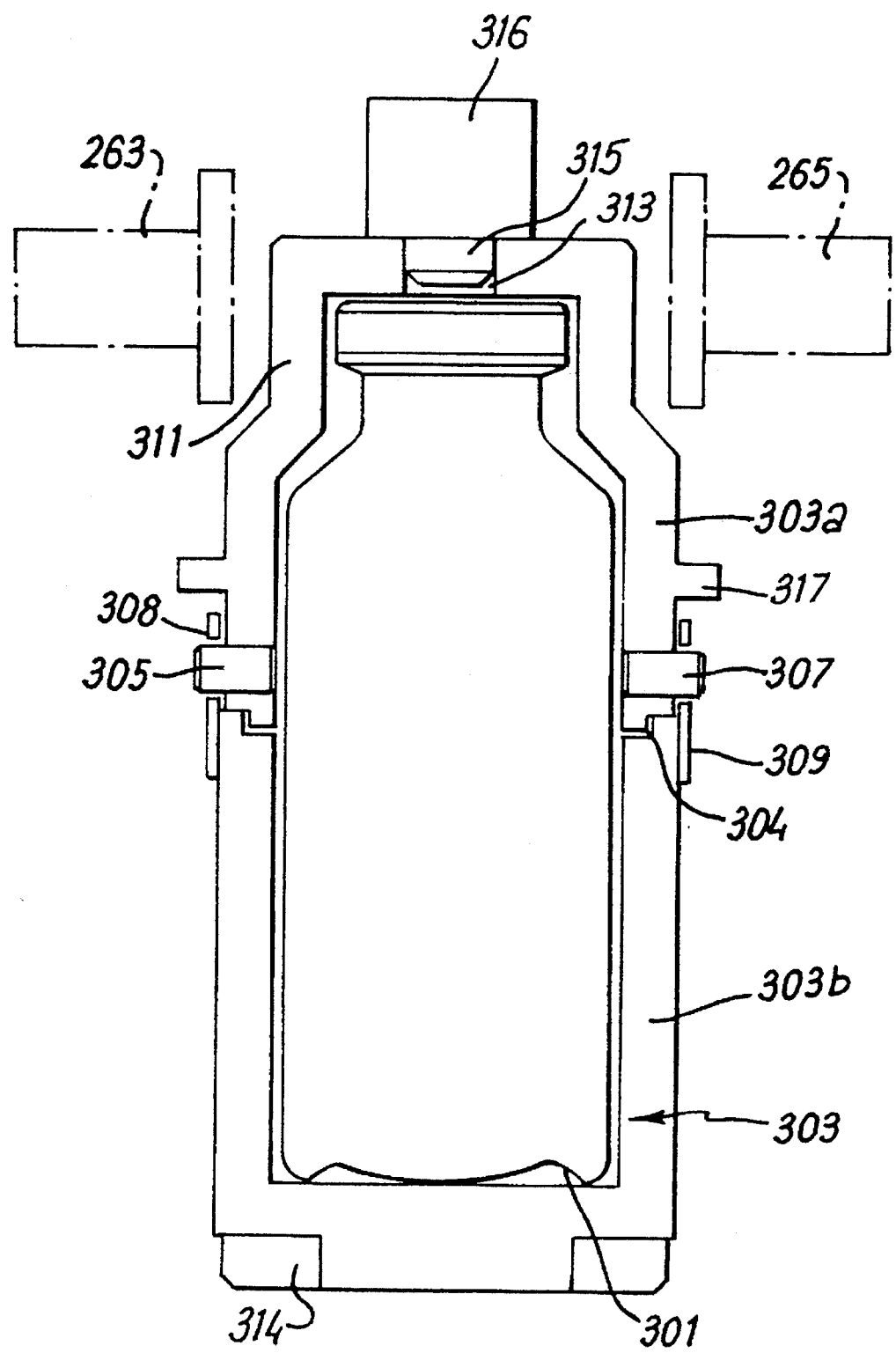
FIG. 16 is a cross-sectional side elevation of an alternative vial and shield for use in the apparatus embodying the invention.

FIG. 16 shows another form of vial and shield therefor alternative to the vial 62 and shield 54 shown in FIG. 6. In FIG. 16 the shield is suitable for picking up and placing by the form of gripper shown in FIGS. 14, 15 indicated by dashed lines and numerals 263 and 265 in FIG. 16. A container or vial 301 is located inside a shield 303 made for example of tungsten. The shield 303 has an upper part 303a and a lower part 303b which are fitted together in a spigotted joint 304. The parts 303a, 303b are retained together by pins 305, 307 located in slots in the upper part 303a and by a retaining ring 309 bonded to the lower part 303b which provides a bayonet-type fitting via a slot 308 over the pins 305, 307. The upper part 303a has a neck portion 311 which conforms in shape to the neck of the container 301 inside. As for the shield 54 the upper part 303a has on its axis an upper aperture 313 which permits access to the container and a rubber cap 315. The part 303b has a recessed base 313 to facilitate storage of the shield 303 and container 301 therein. A shielding lid 316 completes the shielding provided by the shield 303.

The shield 303 and container 301 therein are used in a manner generally similar to the shield 54 and vial 62 of FIG. 6 as described hereinbefore except that the shield 303 is picked up on the sides of the neck portion 311 by gripping by the flat jaws, e.g. 263, 265 of the robot device. The shield 303 has a flange 317 on its upper part 303a which acts as a stop when the container is presented to the radioisotope source to enable radioisotope containing liquid to be drawn therein from the source.

The syringes 48a used for multi-dose preparation may have a capacity suitable to receive 5 ml from the stock solution and the syringes 48c used for patient doses may have a capacity suitable to receive 1 ml from the multi-dose solution (via a vial 62). Thus, the respective ports in the filling station 32 shown in FIGS. 9 and 10 may be required to receive and hold syringes of 1 ml and 5 ml capacity and optionally also syringes of an intermediate size, e.g. 2 ml.

In an alternative embodiment (not shown) having a single port adapted to receive, hold and operate syringes of different size, the construction may generally be similar to one of the ports shown in FIGS. 9 and 10, i.e. one port of the station 32 which receives, holds and operates one syringe 94 and locates and one container 54 therewith. However, in the alternative embodiment the abutment members corresponding to the shoulders 96a and 98a are adjustable in separation distance by a motorised drive and the slots in these members have spring-loaded clamps, e.g. with plastic jaws, to accommodate different syringe diameters. The different syringes are operated in the same way in a similar manner to that described above.

We claim:

1. A dispensing apparatus comprising a robot device having gripping means presentable to a plurality of stations, each station being adapted to provide an operation in a sequence of operations such as to produce a measured quantity or dose from a supply of a hazardous substance, and one of the stations comprising a multi-syringe receiving and filling station comprising syringe receiving means capable of receiving and holding syringes of different sizes each adapted to contain a said substance, the said station having means for operating each syringe when located at that station.

2. An apparatus as in claim 1 and wherein the syringe receiving means comprises a single port having adjustable locating means adapted to locate syringes of different sizes.

3. An apparatus as in claim 1 and wherein the syringe receiving means comprises a plurality of ports in parallel each having locating means to locate a different selected syringe.

4. Apparatus as in claim 2 and wherein the said station further comprises a container receiver and means for moving the locating means relative to the container receiver whereby when a syringe is held by the locating means its end may be moved toward a container when on the container receiver.

5. Apparatus as in claim 4 and wherein the means for moving is such that a needle when held on a syringe held on the locating means can be moved to enter a container on the container receiver.

6. An apparatus as in claim 4 and wherein the said station further includes means for equalising the air pressure in the syringe and the container when one is inserted into the other.

7. An apparatus as in claim 4 and wherein the said station also includes means for rotating the syringe locating means relative to the container receiver whereby in use the container may be arranged after rotation to be above the syringe.

8. Apparatus as in claims 4 and wherein syringes for use in connection with the apparatus each have shoulders for supporting the syringe and a plunger for drawing liquid into and ejecting liquid from the syringe and the said one station comprises a mechanism providing at the syringe port:

(a) means for locating the shoulders of the selected syringe in use at the port;

(b) means for locating and operating in use the plunger of the syringe;

(c) means for locating in use the upper end of a container and for resiliently opposing relative movement of the container and syringe; and (d) means for inverting the container relative to the syringe.

9. Apparatus as claimed in claim 1 and further comprising a container and a shielded receptacle for the container, the receptacle being shaped at an upper end thereof to cooperate with the gripping means.

10. Apparatus as claimed in claim 9 and wherein the receptacle has a base with at least one recess therein, and another of the stations having means for locating the receptacle.

11. Apparatus as claimed in claim 9 and wherein the receptacle has a cap, and the cap has a substantially axial hole therethrough for allowing access to the container.

12. Apparatus as claimed in claim 9 and wherein a further said station comprises monitoring means for locating a container or a said syringe, and for moving the container or the said syringe to a radioactivity detector located at a different level so as to monitor the container or the syringe.

13. Apparatus as claimed in claim 8 and wherein means are provided for controlling the apparatus in a predetermined sequence of operations including operations at the said stations.

14. Apparatus as claimed in claim 13, wherein the predetermined sequence includes operation of means for moving the locating means relative to the corresponding container receiver in the syringe receiving and filling station.

15. Apparatus as claimed in claim 13 and wherein the predetermined sequence includes a plurality of operations of the plunger locating and operating means and thereby of the plunger of a syringe so as to expel air or liquid as appropriate from the syringe.

16. Apparatus as claimed in claim 1 and wherein the gripping means comprise opposing first jaw members, and opposing second jaw members projecting from the first jaw members.

17. Apparatus as claimed in claim 16 and wherein the robot device includes a wrist element for rotating the gripping means whereby items may be picked either by the first law members or by the second law members.

18. Apparatus as in claim 13 and wherein the said sequence of operations comprise the procedures of:

(a) elution of material from a concentrated source to a user stock source;

(b) preparation of different doses from the user stock source; and (c) preparation of individual patient doses from appropriate selected doses.

19. Apparatus as in claim 18 and wherein the said elution procedure comprises the steps of (a) an empty shielded stock bottle being picked up by the robotic device;

(b) the shielded stock bottle being moved by the robotic device to a turnover station and the bottle being turned over by the robotic device and then regripped by the robotic device;

(c) the shielded stock bottle being presented by the robotic device to a port from which the radioisotope or other hazardous material at its source may be drawn; and a quantity of the hazardous material being drawn into the stock bottle;

(d) the shielded stock bottle and its contents being transferred by the robotic device to a storage station where the bottle is stored until required for use.

20. Apparatus as in claim 18 and wherein the said procedure of preparation of different doses from the user stock source comprises the steps of:

(a) a syringe being collected by the robotic device the syringe having a needle fitted therein;

(b) the syringe being placed and fitted in an appropriate port in the filling station by the robotic device;

(c) the stock bottle with eluted stock solution being placed below the syringe at the filling station by the robotic device;

(d) the stock bottle being raised at the filling station so that the syringe needle enters the stock bottle;

(e) the syringe and stock bottle being rotated relative to one another at the filling station so that the stock bottle is above the syringe;

(f) a quantity of the stock solution being withdrawn by operation of the syringe at the filling station from the stock bottle into the syringe;

(g) the stock bottle being returned by the robotic device to its position on a storage tray;

(h) a multi-dose preparation vial being placed by the robotic device beneath the syringe; and (i) the contents of the syringe being transferred into the vial by operation of the syringe at the filling station.

* * * * *